US012569492B1

(12) United States Patent
Moheno

(10) Patent No.: US 12,569,492 B1
(45) Date of Patent: Mar. 10, 2026

(54) IMMUNO-THERAPEUTIC CHEMICAL COMPOSITIONS AND USES THEREOF

(71) Applicant: Phillip Moheno, San Diego, CA (US)

(72) Inventor: Phillip Moheno, San Diego, CA (US)

( * ) Notice: Subject to any disclaimer, the term of this patent is extended or adjusted under 35 U.S.C. 154(b) by 0 days.

(21) Appl. No.: 19/280,031

(22) Filed: Jul. 24, 2025

Related U.S. Application Data

(60) Provisional application No. 63/739,478, filed on Dec. 27, 2024.

(51) Int. Cl.
| | |
|---|---|
| *A61K 31/519* | (2006.01) |
| *A61K 31/51* | (2006.01) |
| *A61K 31/714* | (2006.01) |
| *A61K 33/06* | (2006.01) |
| *A61K 33/30* | (2006.01) |
| *A61K 45/06* | (2006.01) |

(52) U.S. Cl.
CPC ............ *A61K 31/519* (2013.01); *A61K 31/51* (2013.01); *A61K 31/714* (2013.01); *A61K 33/06* (2013.01); *A61K 33/30* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 6,358,953 B1 * | 3/2002 | Moheno | ............... | C07D 475/04 514/249 |
| 2015/0010509 A1 | 1/2015 | Moheno | | |
| 2016/0015711 A1 * | 1/2016 | Moheno | ............... | A61K 31/519 514/249 |
| 2017/0143720 A1 | 5/2017 | Moheno | | |

FOREIGN PATENT DOCUMENTS

WO    WO-2012147003 A1 *  11/2012  ............. A61P 43/00

OTHER PUBLICATIONS

Carvalho et al. "Vitamin B12 (cobalamin) supplementation for the management of autoimmune rheumatic diseases: potential indications and opportunity for future research," Rheumatology International (2024) 44:743-744 published Oct. 17, 2023. (Year: 2024).*

Simkin, "Oral Zinc Sulphate in Rheumatoid Arthritis," The Lancet vol. 308, Issue 7985, Sep. 11, 1976, pp. 539-542 (Year: 1976).*

Salesi "Efficacy of Vitamin D in patients with active rheumatoid arthritis receiving methotrexate therapy," Rheumatol Int (2012) 32: 2129-2133. (Year: 2012).*

Moheno et al. "Immunopterin: A prospective therapy and preventative to fight COVID-19?" De Gruyter 2022. (Year: 2022).*

Moheno, Phillip, "A Review of the Development of Calcium Pterins and (250:1 Mol:Mol) Calcium Folate for the Immunotherapy of Certain Diseases"; Drug Designing; Open Access; vol. 6. Issue 1 (2017).

Moheno, Phillip, "Observational study of Calcium Folate"; Open Science Journal of Pharmacy and Pharmacology 2(3) 14-18 (2014).

Moheno, Phillip, "Immunopterin: A prospective therapy and preventative to fight COVID-19"; De Gruyter 33: 11-20 (2022).

* cited by examiner

*Primary Examiner* — Jeffrey S Lundgren
*Assistant Examiner* — Michael J Schmitt
(74) *Attorney, Agent, or Firm* — ARC IP Law, PC; Joseph J. Mayo

(57) ABSTRACT

Disclosed herein are methods for the treatment of cancer and inflammatory-based diseases and disorders, such as coronavirus colds and as a therapy against COVID-19. Immuno-Folate has been shown to reduce the incidents of colds and flus. In one embodiment is a method of treating cancer comprising administration of ImmunoFolate. In another embodiment is a method of treatment inflammatory-based disease and disorders comprising administration of ImmunoFolate.

10 Claims, 2 Drawing Sheets

Figure 1:
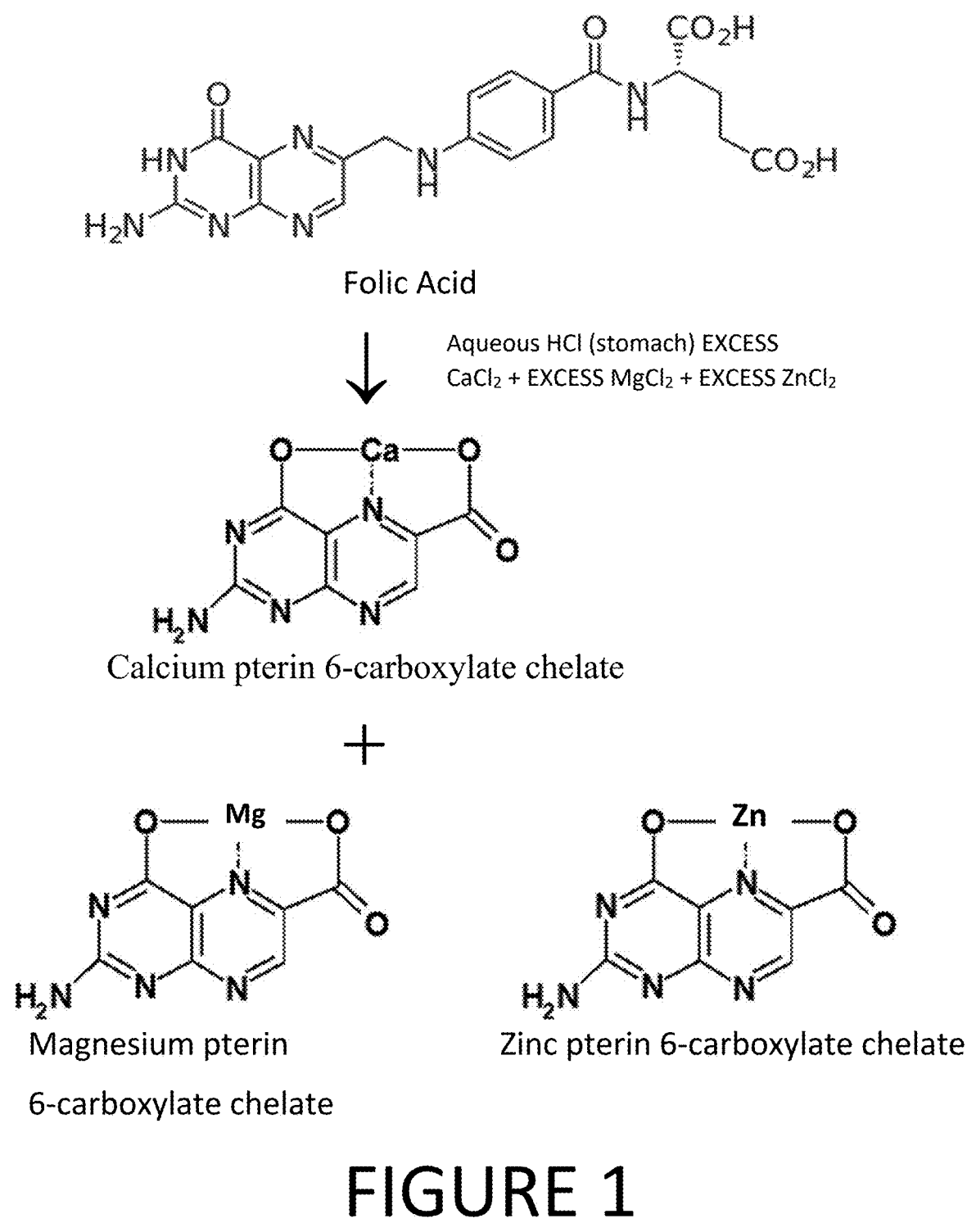

Folic Acid

Aqueous HCl (stomach) EXCESS
$CaCl_2$ + EXCESS $MgCl_2$ + EXCESS $ZnCl_2$

Calcium pterin 6-carboxylate chelate

+

Magnesium pterin
6-carboxylate chelate

Zinc pterin 6-carboxylate chelate

Wherein 4M is any metal;

NM is any non-metal group including:
hydrogen, alkyl, perhaloalkyl, carboxyl, amido, carboxamido, oxo,
carboxy esters, amino, halogen, haloalkyl, hydroxy, alkoxy, azido,
acylalkyl, hydroxyalkyl, -C(O)H, aryl, alicyclic, aralkyl, thioalkyl,
sulfhydryl (-SH), sulfonyl ($SO_2^{-3}$), -CN, perhaloalkoxy, acyl, and null;
and n is a whole number.

IMMUNO-THERAPEUTIC CHEMICAL COMPOSITIONS AND USES THEREOF

This patent application claims the benefit of U.S. Provisional Patent Application 63/739,478 filed 27 Dec. 2024, the specification of which is hereby incorporated herein by reference.

BACKGROUND

Previously it has been reported that ImmunoPterin (IP) (Folic Acid, calcium chloride) as a therapeutic treatment against coronavirus colds and as a therapy against COVID-19. ImmunoPterin has been shown to reduce the incidents of colds and flus. ImmunoPterin is also identified as Calcium Folate, and consists of a combination of folic acid and Calcium chloride. However, there remain derivative or similar chemical compositions that have yet to be disclosed that provide additional and/or more effective therapeutic treatments. These similar or derivative chemical compositions and their therapeutic treatments are described within this application.

BRIEF SUMMARY

Aspects and advantages of the disclosure will be set forth in part in the following description, or may be obvious from the description, or may be learned through practice of the disclosure. Various embodiments provide ophthalmic therapeutic treatment compositions.

In one embodiment of the disclosure, a method of treating cancer comprising administration of a composition comprising of "ImmunoFolate", is provided, wherein ImmunoFolate comprises.

folic acid, calcium chloride ($CaCl_2$) or hydrates thereof or both, and at least one of magnesium chloride ($MgCl_2$) or hydrates thereof or both, Vitamin B12.

In one embodiment of the disclosure, a method of treating cancer comprising administration of a composition comprising of ImmunoFolate, wherein ImmunoFolate has a greater therapeutic efficacy as compared to administration of Calcium Folate, is provided.

In one embodiment of the disclosure, a method of treating cancer comprising administration of a composition comprising of ImmunoFolate, wherein ImmunoFolate is administered through oral, parenteral, intravenous, subcutaneous, intrathecal, intramuscular, buccal, intranasal, epidural sublingual, pulmonary, local, rectal, or transdermal administration, is provided.

In one embodiment of the disclosure, a method of treating cancer comprising administration of a composition of ImmunoFolate plus zinc, is provided.

In one embodiment of the disclosure, a method of treating cancer comprising administration of a composition of ImmunoFolate plus zinc, wherein ImmunoFolate plus zinc is administered through oral, parenteral, intravenous, subcutaneous, intrathecal, intramuscular, buccal, intranasal, epidural sublingual, pulmonary, local, rectal, or transdermal administration, is provided.

In one embodiment of the disclosure, a method of treating an inflammatory-based disease or disorder in a subject comprising administration of a composition of ImmunoFolate, is provided.

In one embodiment of the disclosure, a method of treating an inflammatory-based disease or disorder in a subject comprising administration of a composition of ImmunoFolate, wherein the ImmunoFolate is administered through oral, parenteral, intravenous, subcutaneous, intrathecal, intramuscular, buccal, intranasal, epidural sublingual, pulmonary, local, rectal, or transdermal administration, is provided.

In one embodiment of the disclosure, a method of treating an inflammatory-based disease or disorder in a subject comprising of administration of a composition comprising of ImmunoFolate plus zinc, is provided.

In one embodiment of the disclosure, a method of treating an inflammatory-based disease or disorder in a subject comprising of administration of a composition comprising of ImmunoFolate plus zinc, wherein the ImmunoFolate plus zinc is administered through oral, parenteral, intravenous, subcutaneous, intrathecal, intramuscular, buccal, intranasal, epidural sublingual, pulmonary, local, rectal, or transdermal administration, is provided.

In one embodiment of the disclosure, a method of treating an inflammatory-based disease or disorder in a subject comprising of administration of a composition comprising of ImmunoFolate plus zinc, wherein the inflammatory-based disease or disorder is arthritis, is provided.

In one embodiment of the disclosure, a method of treating an inflammatory-based disease or disorder in a subject comprising of administration of a composition comprising of ImmunoFolate plus zinc, wherein the inflammatory-based disease or disorder is arthritis, wherein the arthritis is osteoarthritis, rheumatoid arthritis, gout, psoriatic arthritis, lupus, or septic arthritis, is provided.

In one embodiment of the disclosure, a method of treating an inflammatory-based disease or disorder in a subject comprising administration of a composition of ImmunoFolate, wherein the inflammatory-based disease or disorder is arthritis, is provided.

In one embodiment of the disclosure, a method of treating an inflammatory-based disease or disorder in a subject comprising administration of a composition of ImmunoFolate, wherein the inflammatory-based disease or disorder is arthritis, wherein the arthritis is osteoarthritis, rheumatoid arthritis, gout, psoriatic arthritis, lupus, or septic arthritis, is provided.

BRIEF DESCRIPTION OF THE FIGURES

A full and enabling disclosure of the present disclosure, including the best mode thereof, directed to one of ordinary skill in the art, is set forth in the specification, which makes reference to the appended drawings in, which:

FIG. 1 provides the stomach chemistry that occurs upon oral ingestion of the formulations of the chemical composition; and, the hypothesized active chelates generated.

FIG. 2 provides additional active modifications of the FIG. 1 chemical compositions wherein:

4M is any metal; and

Figure 2:
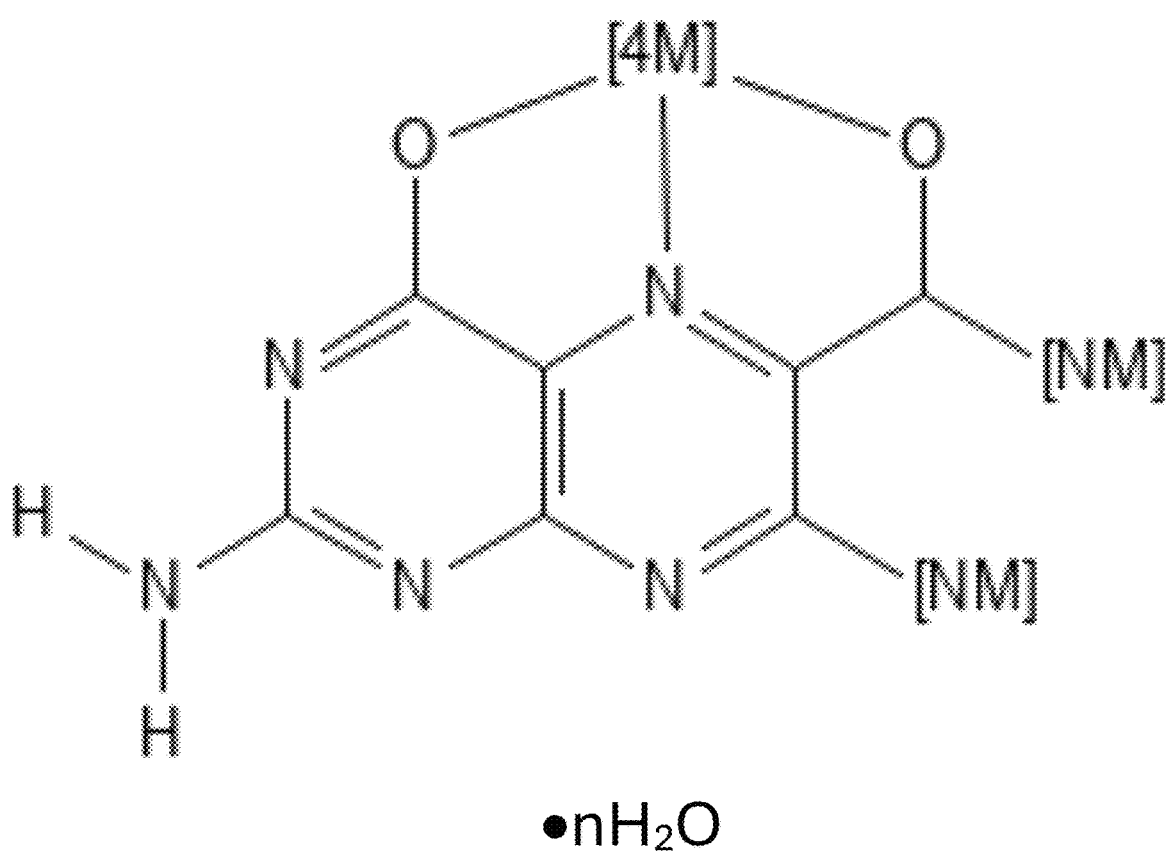

NM is any non-metal group including:

hydrogen, alkyl, perhaloalkyl, carboxyl, amido, carboxamido, oxo, carboxy esters, amino, halogen, haloalkyl, hydroxy, alkoxy, azido, acylalkyl, hydroxyalkyl, —C(O)H, aryl, alicyclic, aralkyl, thioalkyl, sulfhydryl (—SH), sulfonyl ($SO_2^{-3}$), —CN, perhaloalkoxy, acyl, and null.

DETAILED DESCRIPTION

Reference now will be made in detail to embodiments of the disclosure, one or more examples of which are illustrated in the drawings. Each example is provided by way of explanation of the disclosure, not limitation of the disclosure. In fact, it will be apparent to those skilled in the art that various modifications and variations can be made in the present disclosure without departing from the scope or spirit of the disclosure. For instance, features illustrated or described as part of one embodiment can be used with another embodiment to yield a still further embodiment. Thus, it is intended that the present disclosure covers such modifications and variations as come within the scope of the appended claims and their equivalents.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

As used herein, including in the claims, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination. Also, as used herein, including in the claims, "or" as used in a list of items (for example, a list of items prefaced by a phrase such as "at least one of" or "one or more of") indicates an inclusive list such that, for example, a phrase referring to "at least one of" a list of items refers to any combination of those items, including single members. As an example, "at least one of: A, B, or C" is intended to cover A, B, C, A-B, A-C, B-C, and A-B-C, as well as any combination with multiples of the same element (e.g., A-A A-A-A, A-A-B, A-A-C, A-B-B, A-C-C, B-B, B-B-B, B B-C, C-C, and C-C-C or any other ordering of A, B, and C).

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

Unless otherwise defined or implied herein, all terms (including technical and scientific terminology) used in this document retain their commonly understood meanings as recognized by those skilled in the relevant field. Furthermore, it is to be understood that terms, including those defined in standard dictionaries, should be interpreted in a manner that is consistent with their usage within the context of the relevant field and this disclosure. These terms should not be construed in an idealized or overly formal sense unless explicitly specified otherwise herein.

A new chemical moiety identified to be ImmunoFolate (IF), which has the components of folic acid, calcium chloride, magnesium chloride has been found to exhibit potent therapeutics effects including anti-inflammatory, antiviral, and antineoplastic properties. The ImmunoFolate formulation can also include Vitamin B1. The ImmunoFolate formulation can also include Vitamin B12. The ImmunoFolate formulation can also include other vitamins as well. ImmunoFolate can be used as a treatment against Covid, the common colds, and the flu along with numerous other similar ailments. The ImmunoFolate formulation can act as an Antiviral and address afflictions such as hepatitis B virus (HBV). The ImmunoFolate formulation can act as an Antimycoplasma (Tuberculosis). The ImmunoFolate formulation can act as an Anti-Diabetes I agent and an Anti-Diabetes II. The ImmunoFolate formulation can act as an Adjunctive Psychotherapeutic. The disclosure can further provide a method of treating an inflammatory-based disease or disorder in a subject comprising administration of a composition comprising of ImmunoFolate formulation. The disclosure can further provide a method of treating an inflammatory-based disease or disorder in a subject comprising administration of a composition comprising of ImmunoFolate formulation, wherein the subjects are human. The disclosure can further provide a method of treating an inflammatory-based disease or disorder in a subject comprising administration of a composition comprising of ImmunoFolate formulation, wherein the subjects are canines or felines.

A second new chemical moiety identified to be ImmunoFolate (IF) plus zinc, which has the components of folic acid, calcium chloride, and Zinc, has been found to exhibit potent therapeutics effects including anti-inflammatory antiviral, and antineoplastic properties. The ImmunoFolate plus zinc formulation can also include Vitamin B1. The ImmunoFolate plus zinc formulation can also include Vitamin B12. The ImmunoFolate plus zinc formulation can also include other vitamins as well. ImmunoFolate plus zinc can be used as a treatment against Covid, the common colds, and the flu along with numerous other similar ailments. The ImmunoFolate plus zinc formulation can act as an Antiviral and address afflictions such as hepatitis B virus (HBV). The ImmunoFolate plus zinc formulation can act as an Antimycoplasma (Tuberculosis). The ImmunoFolate plus zinc formulation can act as an Anti-Diabetes I agent and an Anti-Diabetes II. The ImmunoFolate plus zinc formulation can act as an Adjunctive Psychotherapeutic. The disclosure can further provide a method of treating an inflammatory-based disease or disorder in a subject comprising administration of a composition comprising of ImmunoFolate plus zinc formulation, wherein the subjects are human. The disclosure can further provide a method of treating an inflammatory-based disease or disorder in a subject comprising administration of a composition comprising of ImmunoFolate plus zinc formulation, wherein the subjects are canines or felines.

Both ImmunoFolate and ImmunoFolate plus zinc can be utilized to treat inflammatory-based disease or disorder is arthritis. Arthritis could mean osteoarthritis, rheumatoid arthritis, gout, psoriatic arthritis, lupus, or septic arthritis.

The optimum daily dosing of the chemical composition is described using "µg" to represent micrograms and "mg" to represent milligrams.

The optimum daily dosing of ImmunoFolate is as follows:

Folic Acid 600 µg $CaCl_2$ (plus hydrates thereof) 50 mg $MgCl_2$ (plus hydrates thereof) 100 mg $ZnSO_4$ (plus hydrates thereof) 8 mg; and Vitamin B12 25 μg The optimum daily dosing of ImmunoFolate without Zinc is as follows:

Folic Acid 600 μg

CaCl2 (plus hydrates thereof) 50 mg

MgCl2 (plus hydrates thereof) 100 mg

Vitamin B12 25 μg

The optimum daily dosing of ImmunoFolate without Zinc and Magnesium is as follows:

Folic Acid 600 μg

CaCl2 (plus hydrates thereof) 50 mg

Vitamin B12 25 μg

Other effective dosing of ImmunoFolate includes a daily dose of the following:

Folic Acid 200-1000 μg

CaCl2 (plus hydrates thereof) 19-106 mg

MgCl2 (plus hydrates thereof) 25 mg-1,000 mg

ZnSO4 (plus hydrates thereof) 2-10 mg

Vitamin B12 10-100 μg

Vitamin D3—5,000 IU

Multivitamins

Taurine—1,000 mg

Alpha Lipoic Acid—600 mg-1200 mg

Vitamin K2 100 μg

GlyNAC [Glycine 1,000 mg+N-Acetyl L-Cysteine 100 mg]

[or GlyNACET [Glycine 1,000 mg+N-Acetyl L-Cysteine Ethyl Ester 100 mg]]

The optimum daily dosing of ImmunoFolate is as follows

Folic Acid 200-1000 μg

CaCl2 (plus hydrates thereof) 19-106 mg

MgCl2 (plus hydrates thereof) 25-1,000 mg $ZnSO_4$ (plus hydrates thereof) 2-10 mg Other effective dosing of ImmunoFolate is as follows includes a daily dose of the following:

Folic Acid 200-1000 μg

CaCl2 (plus hydrates thereof) 19-106 mg

MgCl2 (plus hydrates thereof) 25-1,000 mg $ZnSO_4$ (plus hydrates thereof) 2-10 mg

SUMMARY OF THE DISCLOSURE

The present disclosure is directed to novel metal Folic Acid complexes of the formula:

$$Y(MX_a \cdot b[H_2O]){:}(\text{Folic Acid})$$

wherein

M is a bivalent metal ion selected from the group consisting of $Ca^{2+}$, $Cu^{2+}$, $Mg^{2+}$, $V^{2+}$, $Cr^{2+}$, $Mn^{2+}$, $Fe^{2+}$, $Co^{2+}$, $Zn^{2+}$, $Mo^{2+}$, $Sr^{2+}$, $Ba^{2+}$, $Ra^{2+}$, $Ru^{2+}$, $Rh^{2+}$, $Pd^{2+}$, $Cd^{2+}$, $Sn^{2+}$, $W^{2+}$, $Re^{2+}$, $Os^{2+}$, $Ir^{2+}$, $Pt^{2+}$, $Si^{2+}$, and $Sm^{2+}$;

M is a metal ion of charge 2+ or greater;

X is an anion of an acid and has a charge of −1 or less when ionized;

a is an integer of from 1 or greater;

b is an integer for all hydrates; and

Y is an integer of from 3 or greater.

Below is Table 1 which provides a complete blood count (cbc) with different measurements wherein the symbol "uL" represents microliters.

TABLE 1

COMPLETE BLOOD COUNT (CBC) DIFFERENT MEASURES
[Standard Ranges]

| | May 11, 2018 While dosing With IP | Feb. 28, 2023 while dosing with IF | Mar. 28, 2023 while dosing with IF |
|---|---|---|---|
| Basophils (Absolute) [0.0-0.2 × 10E3/uL] | 0.063 | 0.1 | 0.07 |
| Eosinophils (Absolute) [0.0-0.4 × 10E3/uL] | 0.032 | 0.1 | 0.17 |
| Lymphocytes (Absolute) [0.7-3.1 × 10E3/uL] | 1.327 | 2.1 | 2.46 |
| Monocytes (Absolute) [0.1-0.9x 10E3/uL] | 0.616 | 0.9 | 0.78 |
| Neutrophils (Absolute) [1.4-7.0 × 10E3/uL] | 5.862 | 6.0 | 4.57 |
| Basophils (%) [Not Established] | 0.8 | 1 | 0.09 |
| Eosinophils (%) [Not Established] | 0.4 | 1 | 2.1 |
| Lymphocytes (%) [Not Established] | 16.8 | 23 | 30.4 |
| Monocytes (%) [Not Established] | 7.8 | 10 | 9.7 |
| White Blood Cells (WBC) [3.4-10.8 10E3/uL] | 7.9 | 9.2 | 8.08 |
| Hematocrit (%) [37.5-51.0%] | 45.2 | 45.5 | 47.3 |
| Hemoglobin [13.0-17.7 g/dL] | 15.6 | 14.9 | 14.8 |
| Mean Corpuscular Hemoglobin [26.6-33.0 pg] | 30.8 | 29.1 | 29.5 |
| Mean Corpuscular Hemoglobin Concentration [31.5-35.7 g/dL] | 34.5 | 32.7 | 31.3 |
| Mean Corpuscular Volume [79-97 fL] | 89.2 | 89 | 94.2 |
| Platelets [150-450 × 10E3/uL] | 300 | 265 | 308 |
| Red Blood Cells [4.14-5.80 × 10E3/uL] | 5.07 | 5.12 | 5.02 |
| Red Cell Distribution Width (%) [11.6-15.4%] | 13.1 | 13.2 | 15.0 |

Below is Table 2 which provides a comprehensive metabolic panel with different measurements.

TABLE 2

COMPREHENSIVE METABOLIC PANEL, BLOOD
[Standard Range]

| | Jan. 3, 2022 While dosing With IP | Feb. 28, 2023 while dosing with IF | Mar. 28, 2023 while dosing with IF |
|---|---|---|---|
| Total Protein and Albumin/Globulin Ratio (A/G) [1.2-2.2] | 1.7 | 1.8 | — |
| Albumin [3.8-4.8 g/dL] | 4.7 | 4.7 | 4.4 |
| Alkaline Phosphatase [44-121 IU/L] | 65 | 63 | — |
| Alanine Transaminase (aka SGPT Test) [0-44 IU/L] | 18 | 31 | — |
| Aspartate Aminotransferase [0-40 IU/L] | 14 | 23 | — |
| Bilirubin, Total [0.0-1.2 mg/dL] | 0.3 | <0.2 | — |
| Blood Urea Nitrogen (BUN) [0-27 mg/dL] | 23 | 22 | 21 |
| BUN/Creatinine Ratio [10-24] | 14 | 15 | 17 |

TABLE 2-continued

COMPREHENSIVE METABOLIC PANEL, BLOOD
[Standard Range]

| | Jan. 3, 2022 While dosing With IP | Feb. 28, 2023 while dosing with IF | Mar. 28, 2023 while dosing with IF |
|---|---|---|---|
| Calcium [8.6-10.2 mg/dL] | 10.2 | 9.9 | 9.9 |
| Chloride [96-106 mmol/L] | 106 | 103 | 104 |
| Carbon Dioxide [20-29 mmol/L] | 27 | 23 | 29 |
| Creatinine [0.76-1.27 mg/dL] | 1.66 H | 1.50 H | 1.20 |
| eGFR (estimated glomerular filtration rate) [>59 mL/min/1.73] | 41 L | 50 L | 59.9 |
| Globulin, Total [1.5-4.5 g/dL] | 2.7 | 2.6 | — |
| Glucose [70-99 mg/dL] | 99 | 100 H | 96 |
| Potassium [3.5-5.2 mmol/L] | 5.3 H | 4.3 | 5.2 |
| Sodium [134-144 mmol/L] | 146 H | 141 | 141.0 |
| Protein, Total, Serum [6.0-8.5 g/dL] | 7.4 | 7.3 | — |

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein but is to be accorded the broadest scope consistent with the principles and novel features disclosed herein.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of treating a subject for a disease or disorder comprising
    cancer,
    an inflammatory-based disease or disorder,
        arthritis,
        osteoarthritis,
        rheumatoid arthritis,
        gout, psoriatic arthritis,
        lupus, or
    septic arthritis,
    a viral infection,
    mycoplasma,
    diabetes type one,
    diabetes type two,
    chronic kidney disease, based upon blood creatinine levels, comprising:
    administration of a composition of ImmunoFolate which comprises:
    folic acid,
    calcium chloride ($CaCl_2$) or hydrates thereof or both, and
    magnesium chloride ($MgCl_2$) or hydrates thereof or both, and
    optionally Vitamin B12;
dosing daily in the following ranges
    Folic acid: 200-1,000 μg,
    $CaCl_2$: 19-106 mg,
    $MgCl_2$: 25-1,000 mg, and
    optionally Vitamin B12: 10-100 μg.

2. The method of claim 1, wherein ImmunoFolate further comprises zinc as zinc sulfate ($ZnSO_4$) or hydrates thereof or both.

3. The method of claim 1, wherein ImmunoFolate further comprises Vitamin B1.

4. The method of claim 1, wherein ImmunoFolate further comprises any combination of Vitamin D3, Vitamin K2, an amino acid, taurine, an antioxidant, alpha-lipoic acid, GlyNAC.

5. The method of claim 1, wherein said dosing daily comprises dosing $ZnSO_4$ in the following ranges:
    $ZnSO_4$: 2-10 mg.

6. The method of claim 1, wherein said dosing daily comprises dosing in the following amounts:
    Folic acid: 800 μg,
    $CaCl_2$: 106 mg,
    $MgCl_2$: 500 mg, and
    optionally Vitamin B12: 25 μg.

7. The method of claim 1, wherein said dosing daily comprises dosing at:
    $ZnSO_4$: 8 mg.

8. The method of claim 1, wherein said dosing daily comprises dosing in the following amounts:
    Folic acid: 600 μg,
    $CaCl_2$: 50 mg,
    $MgCl_2$: 100 mg.

9. The method of claim 1, wherein the ImmunoFolate is administered through oral, parenteral, intravenous, subcutaneous, intrathecal, intramuscular, buccal, intranasal, epidural sublingual, pulmonary, local, rectal, or transdermal administration.

10. The method of claim 1, wherein the subject is human, canine or feline.

* * * * *